United States Patent
Czupski et al.

(10) Patent No.: US 6,174,415 B1
(45) Date of Patent: Jan. 16, 2001

(54) CHLORINATING SIDE CHAINS OF AROMATIC COMPOUNDS

(75) Inventors: Leonard M. Czupski, Getzville; C. Duncan Rhodes, Lewiston; George J. Bushey, Tonowanda; Mark E. Lindrose, Buffalo, all of NY (US)

(73) Assignee: Occidental Chemical Corporation, Dallas, TX (US)

(*) Notice: Under 35 U.S.C. 154(b), the term of this patent shall be extended for 0 days.

(21) Appl. No.: 09/314,298

(22) Filed: May 19, 1999

(51) Int. Cl.$^7$ .................................................. C07C 17/00
(52) U.S. Cl. ......................................................... 204/157.99
(58) Field of Search .................... 204/157.15, 157.99, 204/158.1

(56) References Cited

U.S. PATENT DOCUMENTS

| | | | |
|---|---|---|---|
| 2,132,361 | * 10/1938 | Osswald et al. | 204/157.99 |
| 2,695,873 | * 11/1954 | Loverde | 204/157.99 |
| 2,810,688 | * 10/1957 | Ivins et al. | 204/157.99 |
| 2,817,632 | * 12/1957 | Mayor | 204/157.99 |
| 2,998,459 | * 8/1961 | Baker et al. | 204/157.99 |
| 3,442,960 | 5/1969 | De Puy et al. | 260/651 |
| 4,029,560 | 6/1977 | Yoshinaka et al. | 204/163 R |
| 4,048,033 | * 9/1977 | Yoshinaka et al. | 204/157.99 |
| 4,056,455 | * 11/1977 | Lademann et al. | 204/157.99 |
| 4,331,821 | 5/1982 | Shchubart et al. | 570/196 |
| 5,157,173 | * 10/1992 | DesJardin et al. | 204/157.97 |

* cited by examiner

Primary Examiner—Kathryn Gorgos
Assistant Examiner—Thao Tran
(74) Attorney, Agent, or Firm—Richard D. Fuerle; Anne E. Brookes

(57) ABSTRACT

Disclosed is a method of chlorinating the side chains of an aromatic compound having the general formula

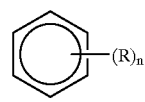

where each R is independently selected from R' or OR', each R' is independently selected from alkyl from $C_1$ to $C_6$, and n is an integer from 1 to 3. Some of the aromatic compound is incompletely α-chlorinated using about 0.1 to about 0.6 equivalents of chlorine per equivalent of the aromatic compound. The α-chlorinated aromatic compound is separated from unreacted aromatic compound and the α-chlorinated aromatic compound is further chlorinated. The two step chlorination of the aromatic compound reduces ring chlorination.

24 Claims, 5 Drawing Sheets

CHLORINATING SIDE CHAINS OF AROMATIC COMPOUNDS

BACKGROUND OF THE INVENTION

This invention relates to a method of chlorinating the side chains of toluene, xylenes, or mesitylenes. In particular, it relates to a method in which a portion of the aromatic compound is incompletely side chain chlorinated, the unreacted aromatic compound is separated from the incompletely side chain chlorinated aromatic compound, and the incompletely side chain chlorinated aromatic compound is further side chain chlorinated.

α,α,α,α',α',α'-hexachloro-m-xylene (HCMX) is used to make fluorinated solvents and other chemicals. It is made by chlorinating m-xylene. (See, for example, U.S. Pat. No. 4,029,560.) While chlorinating m-xylene is effective in making HCMX, it can result in 40 to 50% of the product being ring chlorinated when run as a continuous process; the ring chlorinated material is disposed of as waste.

SUMMARY OF THE INVENTION

We have discovered that ring chlorination of toluene, xylenes, and mesitylenes is greatly reduced if unreacted aromatic compound is removed after some of it has been chlorinated. In our invention, we partially chlorinate only a portion of the aromatic compound, then separate and recycle the unreacted aromatic compound. The partially chlorinated aromatic compound is then further chlorinated. This procedure chlorinates the side chains of aromatic compounds with the production of less than 12% ring chlorinated compounds when run as a continuous process.

We have found that it is primarily the unreacted aromatic compound that is ring chlorinated and that once aromatic compound is at least partially side chain chlorinated, it is protected from ring chlorination. While we do not understand the mechanism and do not wish to be bound by any theories, we believe that the side chain chlorinated aromatic compound may help catalyze the ring chlorination of unreacted aromatic compound.

Ring chlorination occurs to a greater extent in metal reactors than in glass reactors. Typically, there is about 15 to about 25% ring chlorination in a 1 L metal-lined reactor, but only about 5 to about 10% ring chlorination under the same conditions in a 1 L glass reactor. Nickel and other metals are known to catalyze ring chlorination. In the prior art process, sequesterants are added to reduce the catalytic effect of metals on ring chlorination. Yet, in the process of our invention, little or no additional ring chlorination occurs in the presence of nickel, even when a sequesterant is not present.

More ring chlorination also occurs if the process is performed continuously, rather than semi-batch (i.e., the aromatic compound is batch, the chlorine is continuous). Typically, there is about 40% ring chlorination in a continuous process, but only about 12% ring chorination under the same conditions in a batch process. That is unfortunate because greater throughput can be achieved using a continuous process. Nevertheless, in the process of this invention the amount of ring chlorination in a continuous process is comparable to the amount of ring chlorination in a prior art batch process.

Finally, the chlorination of aromatic compounds results in the formation of dimers and trimers, which have no value and must be disposed of. We have found that vacuum distilling the product greatly reduces the formation of dimers and trimers.

Figure 1:
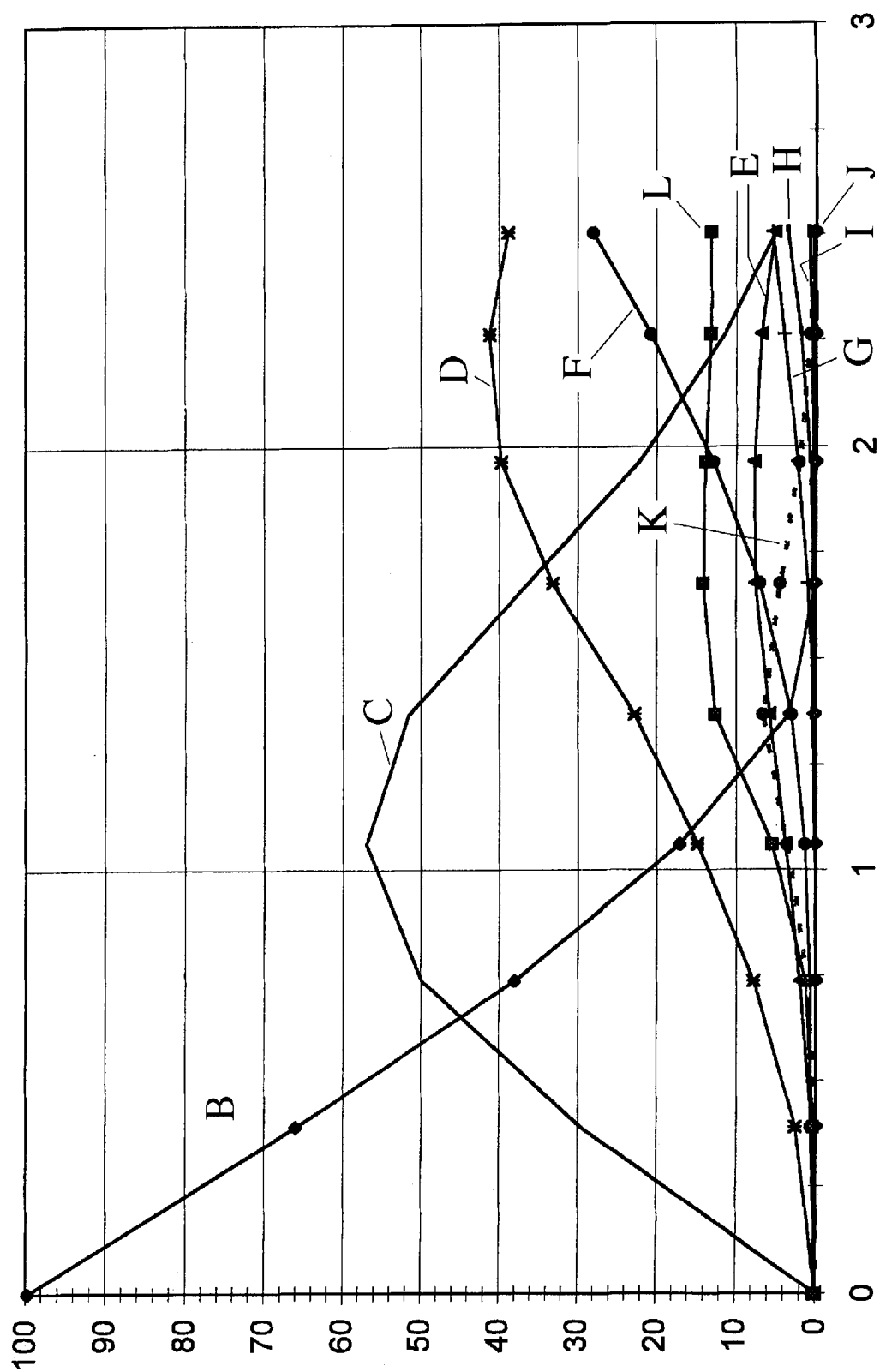
FIG. 1 is a graph showing the changing composition of a reaction mixture as m-xylene is photochlorinated using a prior art semi-batch process in a reactor lined with nickel.

In the drawings, the left ordinate is GC area % and the abscissa is time in hours, except in FIG. 1, where it is the number of chlorines on the m-xylene. The right ordinate in FIGS. 2 to 5 is number of a chlorines on the side chain (line A). Line B is m-xylene, line C is α-chloro-m-xylene, line D is α,α'-dichloro-m-xylene, line E is α,α-dichloro-m-xylene, line F is α,α,α'-trichloro-m-xylene, line G is α,α,α',α'-tetrachloro-m-xylene, line H is α,α,α,α'-tetrachloro-m-xylene, line I is α,α,α,α',α'-pentachloro-m-xylene, line J is HCMX, line K is mono ring chlorinated m-xylene, and line L is all other chlorinated m-xylene derivatives.

DESCRIPTION OF THE PREFERRED EMBODIMENTS

Aromatic compounds that can be side chain chlorinated according to the process of this invention have the general formula:

where each R is independently selected from R' or OR', each R' is independently selected from alkyl from $C_1$ to $C_6$, and n is an integer from 1 to 3. Toluene, xylenes, and mesitylenes are included within the scope of the general formula. Xylenes are preferred, especially m-xylene, due to its commercial importance.

In the first step in the process of this invention, a portion of the aromatic compound is side chain chlorinated by sparging into it at least about 0.1 equivalents of chlorine gas per equivalent of the aromatic compound. If less chlorine is used, too much unreacted aromatic compound has to be recycled. More chlorine may increase the amount of ring chlorination, so that less than about 0.6 equivalents should normally be used; preferably, about 0.4 to about 0.6 equivalents of chlorine gas are used per equivalent of aromatic compound. The chlorination temperature will depend upon the aromatic compound being chlorinated, but generally a temperature of about 100° C. to about reflux can be used; the preferred temperature range is about 120 to about 140° C. If a semi-atch process is used, more chlorine is fed into the reactor at the beginning of the reaction to help decrease ring formation. On the other hand, too much chlorine may entrain unreacted aromatic compound and carry it into the condenser where it is likely to be ring chlorinated.

The generation of chlorine free radicals is needed for side chain chlorination. This can be achieved by the addition of a chlorine free radical generator, such as various azo compounds and peroxides, e.g., di(tert-alkylperoxy) ketals or di-tert-alkylperoxides. Azobisnitrile, sold by DuPont as "Vazo" is preferred. About 0.05 to about 0.3 wt % of a free radical generator can be used. Chlorine free radicals can also be made by photochlorination, e.g., exposing the chlorine to ultraviolet light. Photochlorination is preferred as it results in a higher yield, it is easier to control the reaction, and no additives remain in the product.

The chlorination reaction can be monitored by measuring the concentration of unreacted aromatic compound or the concentration of the side chain chlorinated product. The proportion of unreacted to reacted aromatic compound can be monitored by gas chromatography (GC).

In the next step of the process of this invention, the unreacted aromatic compound is separated from the side chain chlorinated aromatic compound. To reduce ring chlorination, the unreacted aromatic compound should be at least 50 mole %, and preferably at least 60 mole %, of the aromatic compounds in the reactor. That is, when the molar percentage of unreacted aromatic compound falls below those percentages, the partially chlorinated aromatic compound is removed and/or additional unreacted aromatic compound is added. Separation is most easily accomplished by distillation of the unreacted aromatic compound, which is normally recycled and rechlorinated. To reduce the formation of dimers and trimers during this initial distillation, it is preferable to use vacuum distillation at a temperature below the temperature at which dimers and trimers begin to form. A distillation temperature of about 100 to about 165° C., depending on the pressure, is usually suitable. Ring chlorinated and overly-chlorinated aromatic compounds can be separated from a chlorinated aromatic compound during this distillation, but it is preferable to remove those substances in the second distillation. Separation by crystallization may also be possible. Unreacted aromatic compound can be recycled.

In the next step of the process of this invention, the incompletely side chain chlorinated aromatic compound is again chlorinated. The chlorination conditions can be similar to the initial chlorination conditions, except that the number of equivalents of chlorine used will depend upon the extent of chlorination desired. If α,α'-dichloro-m-xylene is being chlorinated to HCMX, for example, about 1.8 to about 2.2 equivalents of chlorine gas are used per equivalent of α,α'-dichloro-m-xylene. Because it is difficult to add the last chlorine to the side chain, if a perchlorinated product is desired, it is preferable to perform this second chlorination in two steps. In the first step, most of the chlorine is added as hereinabove-described. The almost perchlorinated product is then placed in a batch reactor where the remaining 1 or 2 chlorines are added to the side chain at a temperature about 20 to about 50° C. higher than the temperature used in the first step.

The final product can be purified by distillation to separate ring chlorinated material and over or under chlorinated compounds from the desired product. For example, to purify HCMX, a distillation temperature of about 190 to about 210° C. is preferred.

The following examples further illustrate this invention.

EXAMPLE 1

Comparative

Into a 1 L Pyrex light well reactor lined with nickel mesh was placed 880 g m-xylene and 225 ppm (by weight, based on weight of m-xylene) of a 10 to 12 carbon chain N,N-dimethylamide sold by Hall Chemical Co. as "Hallcomid" (a sequesterant used to reduce the catalytic effect of metals in promoting ring chlorination). The reactor was heated to 120° C. and 400 g/hr of chlorine gas was sparged in. The reactor was exposed to a 100 Watt mercury vapor ultraviolet light.

FIG. 1 shows the results. This example shows that about 13% ring chlorinated m-xylene was produced. It also shows that no further ring chlorination occurred after all the m-xylene had been chlorinated (i.e., line L did not rise after line B fell to zero).

EXAMPLE 2

Example 1 was repeated using 250 ppm "Hallcomid," nickel mesh, and 692 g of a feed of m-xylene. The reactor was heated to 120 to 136° C. and 286 g/hr of chlorine gas was sparged in. Xylene flow was started at 1 at a rate of 1150 g/hr to begin the continuous phase of the run. Chlorine flow was stopped at 2 to change chlorine cylinders. Xylene flow was stopped at 3 and chlorine xylene flows were restarted at 4.

Figure 2:
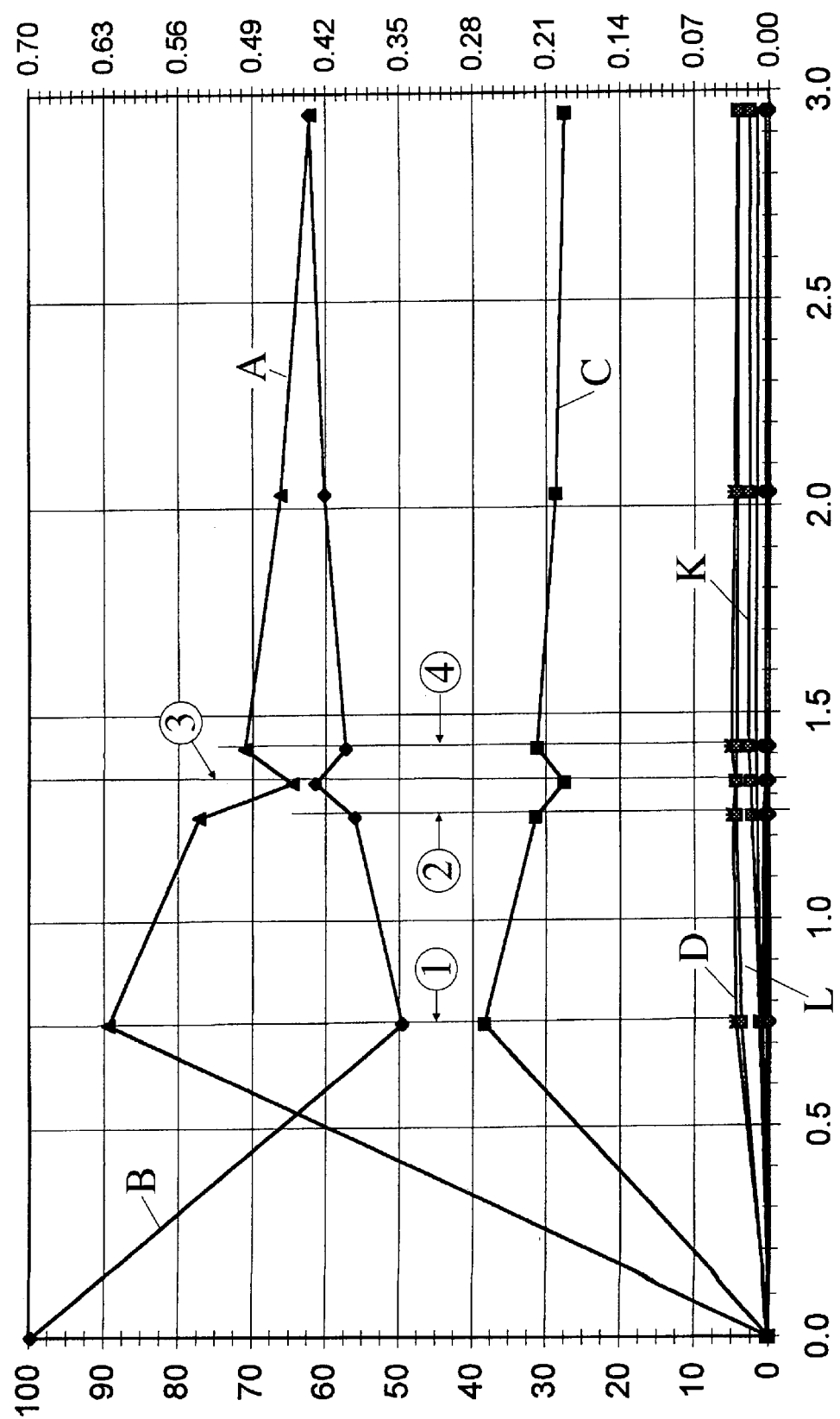
FIG. 2 is a graph showing the changing composition of a reaction mixture as m-xylene is photochlorinated using a continuous process according to this invention in the presence of nickel.

FIG. 2 presents the results and shows that ring chlorination was only about 2–3%.

EXAMPLE 3

Figure 3:
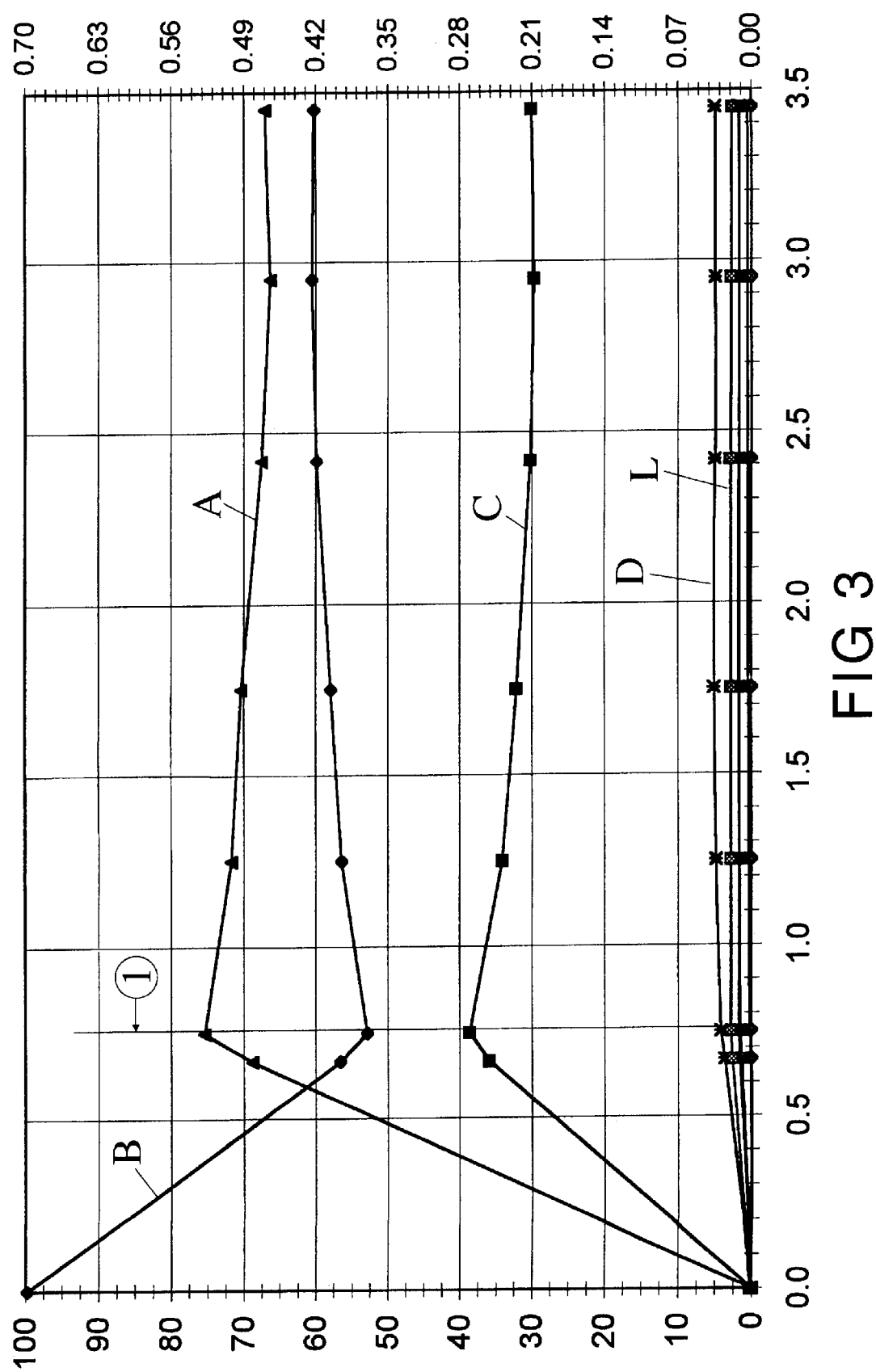
FIG. 3 is a graph showing the changing composition of a reaction mixture as m-xylene is photochlorinated using a continuous process according to this invention in an all glass system.

Example 2 was repeated without the nickel at 120 to 130° C. Xylene flow was started at 1 to begin the continuous process. FIG. 3 presents the results and shows that ring chlorination was only about 1–2%.

EXAMPLE 4

The feed for this example consisted of 98.5% α-chloro-m-xylene containing 1.35 GC area % ring chlorinated m-xylene. Example 2 was repeated using 250 ppm "Hallcomid," nickel mesh, and 250 g of the feed. The photoreactor was heated to 134° C. and 96 g/hr of chlorine gas was sparged in.

Figure 4:
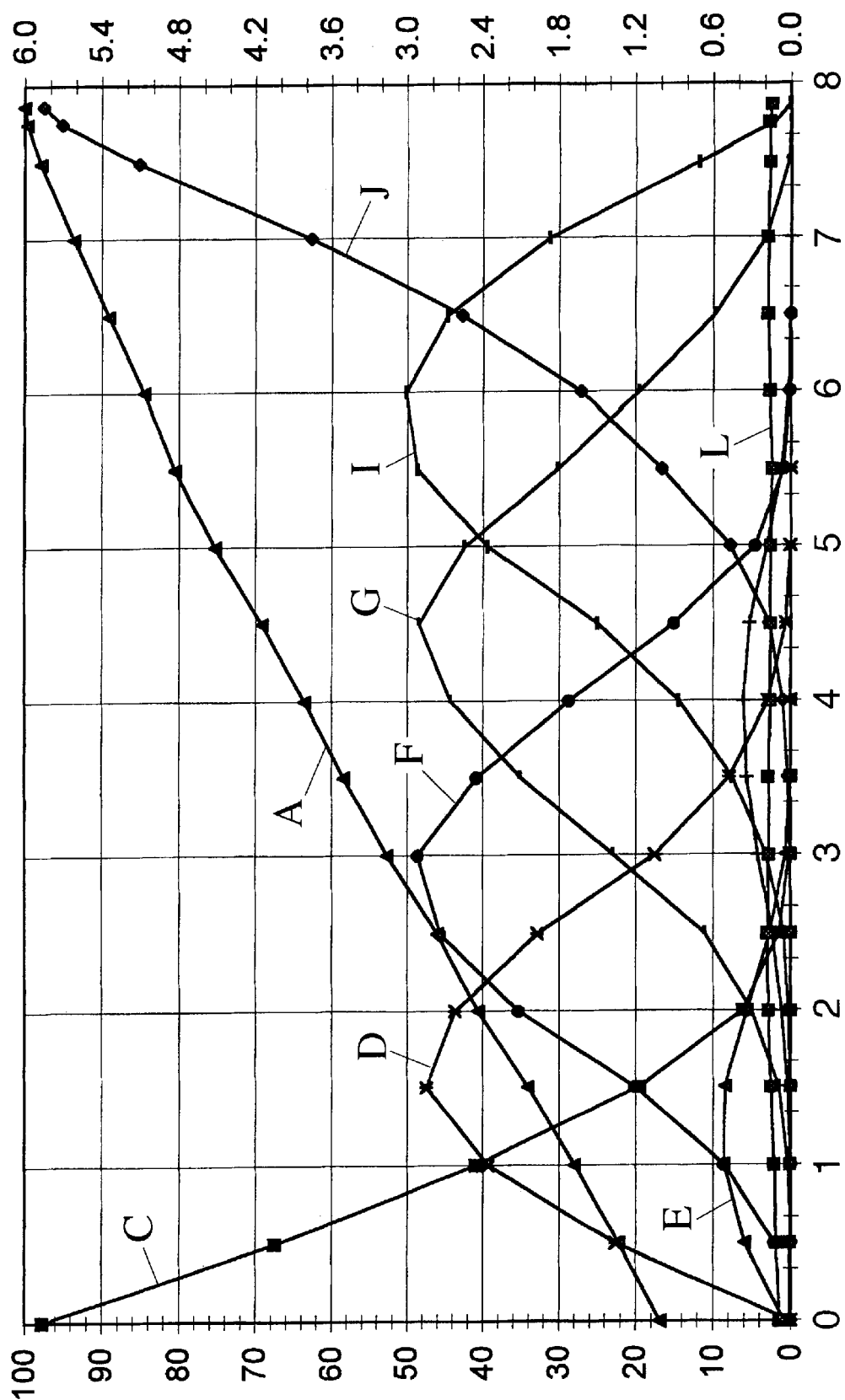
FIG. 4 is a graph showing the changing composition of a reaction mixture as α-chloro-m-xylene is photochlorinated using a semi-batch process according to this invention.

FIG. 4 presents the results and shows that ring chlorination increased only about 1% over the feed.

EXAMPLE 5

Example 4 was repeated as a continuous process using no sequesterant and about 1.5 ml/min of 73 wt % α-Cl-m-xylene and 10 wt % other non-side chain chlorinated xylene compounds as the feed. The reactor was heated to 140 to 150° C. and 300 g/hr of chlorine gas was sparged in. The chlorine and chlorinated m-xylene feeds were started at 1.

Figure 5:
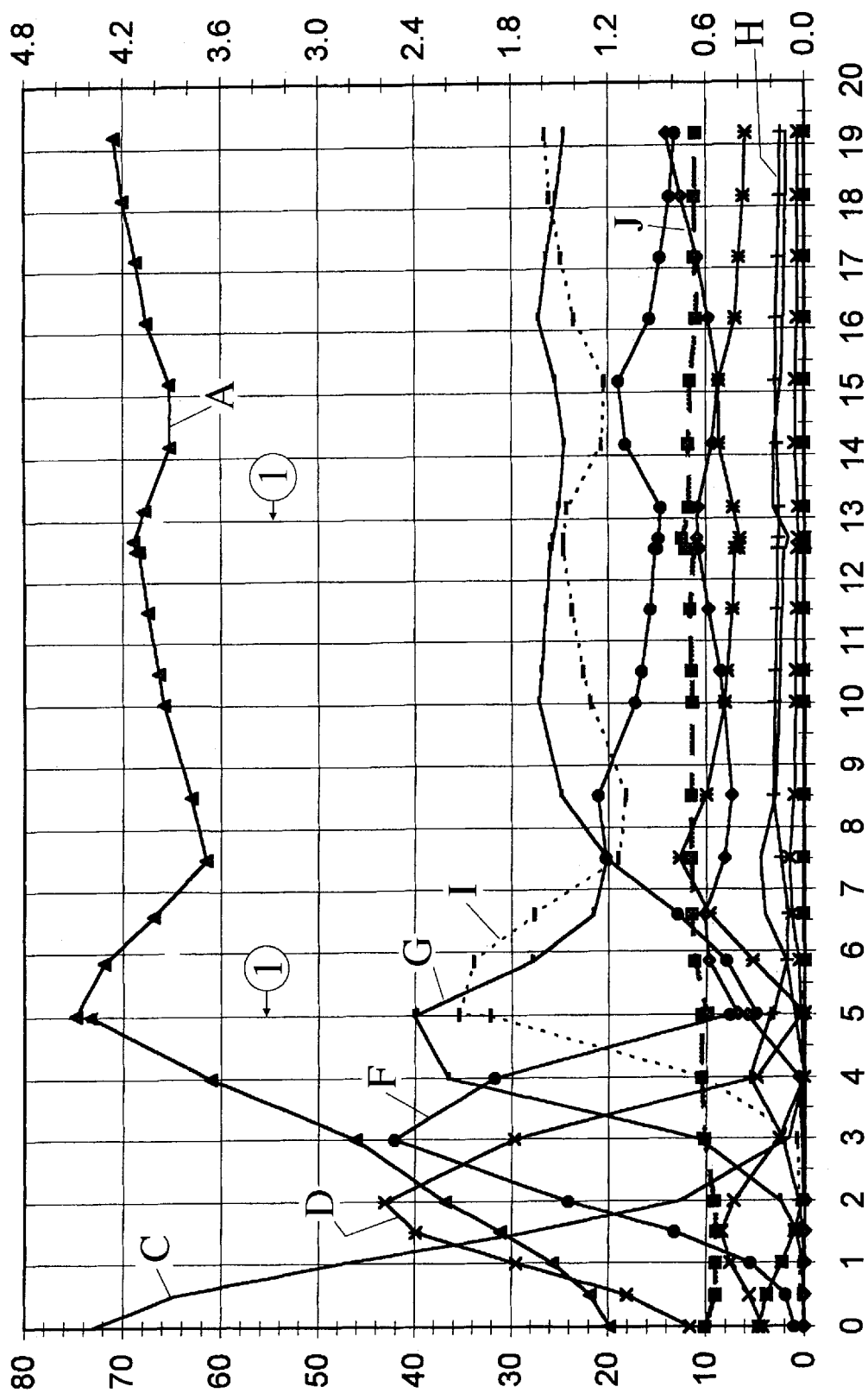
FIG. 5 is a graph showing the changing composition of a reaction mixture as α-chloro-m-xylene is photochlorinated using a continuous process according to this invention.

FIG. 5 presents the results and shows that ring chlorination increased only about 1 % over the feed, even in the presence of nickel with no sequesterant.

We claim:

1. A method of side chain chlorinating an aromatic compound having the general formula

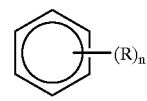

where each R is independently selected from R' or OR', each R' is independently selected from alkyl from $C_1$ to $C_6$, and n is an integer from 1 to 3, comprising partially α-chlorinating only a portion of said aromatic compound with at least about 0.1 equivalents of chlorine per equivalent of said aromatic compound;

(B) separating said partially α-chlorinated aromatic compound from unreacted aromatic compound before said unreacted aromatic compound falls below 50 mole % of said unreacted aromatic compound plus said partially α-chlorinated aromatic compound; and (C) further chlorinating said partially α-chlorinated aromatic compound.

2. A method according to claim 1 wherein said unreacted aromatic compound is recycled to step (A).

3. A method according to claim 1 wherein R' is $CH_3$.

4. A method according to claim 1 wherein n is 2.

5. A method according to claim 1 wherein said aromatic compound is m-xylene.

6. A method according to claim 1 wherein step (B) is performed by distilling off said unreacted aromatic compound.

7. A method according to claim 6 wherein said distilling is vacuum distilling at a temperature below the temperature at which dimers and trimers begin to form.

8. A method according to claim 1 wherein said chlorination in steps (A) and (C) are photochlorinations.

9. A method according to claim 1 wherein a chlorine free radical initiator is used to chlorinate said aromatic compound in steps (A) and (C).

10. A method according to claim 1 performed as a continuous process.

11. A method according to claim 1 performed as a semi-batch process.

12. A method according to claim 1 wherein the amount of chlorine used in step (A) is less than about 0.6 equivalents per equivalent of said aromatic compound.

13. A method according to claim 1 wherein said α-chlorinating is performed in the presence of nickel and the absence of a sequesterant.

14. A method according to claim 1 including the additional last step of distilling said further chlorinated α-chlorinated aromatic compound.

15. A method of chlorinating the side chain of an aromatic compound selected from the group consisting of toluene, o-xylene, m-xylene, p-xylene, and mesitylene comprising, (A) heating in a reactor to about 100° C. to reflux a composition consisting essentially of said aromatic compound;

(B) sparging about 0.1 to about 0.6 equivalents of chlorine gas into said aromatic compound per equivalent of said aromatic compound;

(C) exposing said chlorine gas to ultraviolet light, whereby chlorine free radicals are formed and some, but not all, of said aromatic compound is partially side chain chlorinated;

(D) distilling off aromatic compound that was not chlorinated in step (C) before it is less than 60 mole % of the total of said partially side chain chlorinated aromatic compound plus said unchlorinated aromatic compound in said reactor;

(E) recycling said distilled off aromatic compound that was not chlorinated to step (A);

(F) sparging chlorine gas into said partially side chain chlorinated aromatic compound; and (G) exposing said chlorine gas to ultraviolet light, whereby chlorine free radicals are formed and said partially side chain chlorinated aromatic compound is further partially side chain chlorinated.

16. A method according to claim 15 performed as a continuous process.

17. A method according to claim 15 performed as a semi-batch process.

18. A method according to claim 17 wherein most of said chlorine gas is added at the beginning of the chlorination.

19. A method according to claim 15 including the additional last step of vacuum distilling the product.

20. A method according to claim 15 wherein said aromatic compound is m-xylene.

21. A method of making α,α,α,α',α',α'-hexachloro-m-xylene comprising, (A) heating a composition consisting essentially of m-xylene to about 120 to about 140° C.;

(B) sparging into said m-xylene about 0.4 to about 0.6 equivalents of chlorine gas per equivalent of m-xylene;

(C) exposing said chlorine gas to ultraviolet light, generating chlorine free radicals and forming some α-chloro-m-xylene;

(D) distilling said m-xylene off said α-chloro-m-xylene before said m-xylene is less than 60 mole % of the total of said m-xylene plus said α-chloro-m-xylene;

(E) recycling said distilled off m-xylene to step (A);

(F) sparging into said α-chloro-m-xylene about 1.8 to about 2.2 equivalents of chlorine gas per equivalent of said α-chloro-m-xylene; and (G) exposing said chlorine gas in step (F) to ultraviolet light, thereby generating chlorine free radicals and forming said α,α,α,α',α',α'-hexachloro-m-xylene.

22. A method according to claim 21 that is performed as a continuous process, except that the last 1 or 2 chlorines are added in a batch process.

23. A method according to claim 21 performed in a metal reactor.

24. A method according to claim 21 including the additional last step of vacuum distilling said α,α,α,α',α',α'-hexachloro-m-xylene to purify it.

* * * * *